United States Patent
Polak

(10) Patent No.: US 9,616,232 B2
(45) Date of Patent: Apr. 11, 2017

(54) ELECTRICALLY EVOKED BRAINSTEM RESPONSE MEASUREMENTS VIA IMPLANT PROSTHESIS

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 282 days.

(21) Appl. No.: 14/314,356

(22) Filed: Jun. 25, 2014

(65) Prior Publication Data

US 2014/0309711 A1   Oct. 16, 2014

Related U.S. Application Data

(63) Continuation of application No. 13/194,114, filed on Jul. 29, 2011, now Pat. No. 8,768,448.

(Continued)

(51) Int. Cl.
*A61B 5/04*    (2006.01)
*A61N 1/00*    (2006.01)
(Continued)

(52) U.S. Cl.
CPC ........ *A61N 1/36135* (2013.01); *A61B 5/0031* (2013.01); *A61B 5/0484* (2013.01);
(Continued)

(58) Field of Classification Search
None
See application file for complete search history.

(56) References Cited

U.S. PATENT DOCUMENTS

| | | | |
|---|---|---|---|
| 5,626,629 A | 5/1997 | Faltys et al. | 607/57 |
| 5,758,651 A | 6/1998 | Nygard et al. | 128/741 |

(Continued)

FOREIGN PATENT DOCUMENTS

| | | | | |
|---|---|---|---|---|
| AU | WO 2009076721 A1 * | 6/2009 | ......... | A61N 1/36032 |
| WO | WO 96/39005 A1 | 12/1996 | ............ | H04R 25/00 |

(Continued)

OTHER PUBLICATIONS

Bahmer et al., "Recording of electrically evoked auditory brainstem responses after electrical stimulation with biphasic, triphasic and precision triphasic pulses," Hearing Research, vol. 259, pp. 75-85, 2010.

(Continued)

*Primary Examiner* — Etsub Berhanu
(74) *Attorney, Agent, or Firm* — Sunstein Kann Murphy & Timbers LLP

(57) ABSTRACT

A method of measuring electrically evoked auditory brainstem responses of a patient or animal body is provided. The method includes surgically implanting an auditory prosthesis having an electrode array, the electrode array positioned either intracochlear or substantially proximate a brainstem of the body. At least one electrode is stimulated in the electrode array. Electrically evoked auditory brainstem responses resulting from said stimulation are recorded using, at least in part, an electrode in the electrode array as a negative electrode, and a positive electrode positioned substantially proximate the vertex of the head of the body.

13 Claims, 5 Drawing Sheets

Related U.S. Application Data

(60) Provisional application No. 61/368,892, filed on Jul. 29, 2010.

(51) Int. Cl.
| | |
|---|---|
| *A61N 1/36* | (2006.01) |
| *A61B 5/00* | (2006.01) |
| *A61B 5/0484* | (2006.01) |
| *A61N 1/05* | (2006.01) |
| *A61B 5/12* | (2006.01) |

(52) U.S. Cl.
CPC ........ *A61B 5/04845* (2013.01); *A61N 1/3606* (2013.01); *A61N 1/36032* (2013.01); *A61B 5/12* (2013.01); *A61B 5/4851* (2013.01); *A61B 5/6868* (2013.01); *A61B 5/7203* (2013.01); *A61N 1/0531* (2013.01); *A61N 1/0541* (2013.01)

(56) References Cited

U.S. PATENT DOCUMENTS

| | | | | |
|---|---|---|---|---|
| 6,289,247 | B1* | 9/2001 | Faltys | A61N 1/37247 607/55 |
| 6,944,502 | B2 | 9/2005 | Charvin et al. | 607/57 |
| 6,950,697 | B2 | 9/2005 | Jordan | 600/544 |
| 7,076,308 | B1 | 7/2006 | Overstreet et al. | 607/57 |
| 7,171,261 | B1 | 1/2007 | Litvak et al. | 600/544 |
| 7,206,640 | B1 | 4/2007 | Overstreet | 607/57 |
| 8,768,448 | B2 | 7/2014 | Polak | 600/544 |
| 2004/0158170 | A1 | 8/2004 | Overstreet et al. | 60/554 |
| 2004/0167586 | A1* | 8/2004 | Overstreet | A61N 1/36032 607/48 |
| 2005/0131272 | A1 | 6/2005 | Waldmann | 600/25 |
| 2006/0089561 | A1 | 4/2006 | Eder et al. | 600/546 |
| 2006/0235332 | A1* | 10/2006 | Smoorenburg | A61N 1/36032 600/559 |
| 2006/0235490 | A1 | 10/2006 | Killian et al. | 607/60 |
| 2006/0287690 | A1 | 12/2006 | Bouchataoui et al. | 607/57 |
| 2007/0118047 | A1 | 5/2007 | Tracey et al. | 600/554 |
| 2007/0150039 | A1 | 6/2007 | Leigh et al. | 607/152 |
| 2009/0254149 | A1 | 10/2009 | Polak | 607/57 |
| 2010/0106218 | A1 | 4/2010 | Botros | 607/57 |
| 2010/0152814 | A1 | 6/2010 | Polak | 607/57 |

FOREIGN PATENT DOCUMENTS

| | | | | |
|---|---|---|---|---|
| WO | WO 2010/055421 | 5/2010 | | A61N 1/05 |
| WO | WO 2011/006204 | 1/2011 | | A61F 11/00 |
| WO | WO 2012/016138 | 2/2012 | | A61F 11/04 |

OTHER PUBLICATIONS

Behr et al., "The High Rate CIS Auditory Brainstem Implant for Restoration of Hearing in NF-2 Patients," Skull Base, vol. 17, No. 2, pp. 91-107, 2007.

Brown et al., "Electrically Evoked Whole Nerve Action Potentials in Ineraid Cochlear Implant Users: Responses to Different Stimulating Electrode Configurations and Comparison to Psychophysical Responses," Journal of Speech and Hearing Research, vol. 39, pp. 453-467, Jun. 1996.

Brown et al., "The Relationship Between EAP and EABR Thresholds and Levels Used to Program the Nucleus 24 Speech Processor: Data from Adults," Ear & Hearing, vol. 21, pp. 151-163, Apr. 2000.

Dillier et al., "Measurements of Neural Adaptation in Subjects with Cochlear Implants," ZNZ Symposium, University of ETH Zurich, 1 page, Oct. 15, 2004.

Gantz et al., "Intraoperative Measures of Electrically Evoked Auditory Nerve Compound Action Potential," The American Journal of Otology, vol. 15, No. 2, pp. 137-144, Mar. 1994.

Gibson et al., "The use of intra-operative electrical auditory brainstem responses to predict the speech perception outcome after cochlear implantation," Cochlear Implants Int., 5 pages, 2009.

Kileny et al., "Electrically Evoked Auditory Brain-Stem Response in Pediatric Patients with Cochlear Implants," Archives of Otolaryngology-Head & Neck Surgery, vol. 120, No. 10, 2 pages, Oct. 1994.

Lorens et al., "Outcomes of Treatment of Partial Deafness With Cochlear Implantation: A DUET Study," The Laryngoscope, vol. 118, pp. 288-294, Feb. 2008.

McMahon et al., "Frequency-Specific Electrocochleography Indicates that Presynaptic and Postsynaptic Mechanisms of Auditory Neuropathy Exist," Ear & Hearing, vol. 29, No. 3, pp. 314-325, 2008.

Miller et al., "An Improved Method of Reducing Stimulus Artifact in the Electrically Evoked Whole-Nerve Potential," Ear & Hearing, vol. 21, No. 4, pp. 280-290, Aug. 2000.

Polak et al., "Evaluation of hearing and auditory nerve function by combining ABR, DPOAE and eABR tests into a single recording session," Journal of Neuroscience Methods, vol. 134, pp. 141-149, 2004.

Polak et al., "Further prospective findings with compound action potentials from Nucleus 24 cochlear implants," Hearing Research, vol. 188, pp. 104-116, 2004.

Von Ilberg, "Electric-Acoustic Stimulation of the Auditory System," ORL, vol. 61, pp. 334-340, 1999.

Wilson, "Better speech recognition with cochlear implants," Letters to Nature, vol. 352, pp. 236-238, Jul. 18, 1991.

International Searching Authority, International Search Report—International Application No. PCT/US2011/045882, dated Dec. 13, 2011, together with the Written Opinion of the International Searching Authority, 11 pages.

The International Bureau of WIPO, Notification Concerning Transmittal of International Preliminary Report on Patentability, International Application No. PCT/US2009/067626, dated Jun. 23, 2011, 10 pages.

Guiraud et al., "Effects of auditory pathway anatomy and deafness characteristics? (1) On electrically evoked auditory brainstem responses", Hearing Research, Elsevier Science Publishers, vol. 223, No. 1-2, pp. 48-60, Dec. 22, 2006.

Haenggeli et al., "Electrically Evoked Compound Action Potential (ECAP) of the Cochlear Nerve in Response to Pulsatile Electrical Stimulation of the Cochlea in the Rat: Effects of Stimulation of High Rates", Audiology, vol. 37, No. 6, pp. 353-371, Nov. 1, 1998.

European Patent Office, Extended European Search Report regarding Application No. 11813242.2-1657 dated Dec. 17, 2014, 10 pages.

\* cited by examiner

ELECTRICALLY EVOKED BRAINSTEM RESPONSE MEASUREMENTS VIA IMPLANT PROSTHESIS

CROSS-REFERENCE TO RELATED APPLICATIONS

This application is a continuation of U.S. application Ser. No. 13/194,114, filed Jul. 29, 2011, which in turn claims priority from U.S. provisional application No. 61/368,892 filed Jul. 29, 2010. Each of the above-described applications is hereby incorporated herein by reference in its entirety.

TECHNICAL FIELD

The present invention relates to measurement of electrically evoked Auditory Brainstem Responses (eABR), and more particularly to measurement of eABR via an implant prosthesis.

BACKGROUND ART

The electrodes of commercially available cochlear implant or auditory brainstem implant (ABI) systems may be used for acute electrical stimulation, obtaining important information about the electrodes itself and/or the implant system, or recording electrically evoked potentials (EEP), such as the compound action potential (CAP). The development of electrically evoked CAP responses enabled measurement of CAP responses via a cochlear implant. However, recordings of objective measurements of various other types of EEP via a cochlear or ABI implant are still problematic.

Evoked potentials include early, middle and late latency auditory responses, as described by Katz J., *Handbook of Clinical Audiology*, Williams & Wilkins 4$^{th}$ Edition, 1994, which is hereby incorporated herein by reference. By definition, the CAP is an alternating current response which is generated by the cochlear end of the VIIIth Cranial Nerve, and it represents the summed response of the synchronous firing of thousands of auditory nerve fibers, as described by: Ferraro et al., *The Use of Electrocochleography in the Diagnosis, Assessment, and Monitoring of Endolymphatic Hydrops*, Otolaryngologic Clinics of North America; 16:1, pp. 69-82, February, 1983; and Hall J. W., *Handbook of Auditory Evoked Responses*, Allyn and Bacon; Needham Heights, Mass., 1992, each of which is hereby incorporated herein by reference. The auditory brainstem response (ABR) is an electrical signal evoked from the brainstem of a human or other mammal by the presentation of a specific signal (Katz, 1994). The first recording of an ABR potential in man was performed by Jewett D. L. et al., *Human Auditory Evoked Potentials: Possible Brain Stem Ccomponents Detected on the Scalp*, Science 1970; 167: p. 1517-8, which is hereby incorporated herein by reference. The relationship of specific wave components of the ABR to the components of the auditory pathway can be represented as follows: wave I: Cochlear Action Potential (CAP), distal CNVIII; wave II: proximal CNVIII; wave III: Cochlear Nuclei; wave IV: Superior Olivary Complex; and wave V: Lateral Lemniscus. The definition of peaks is described in Jewett D. L. et al., *Auditory-evoked Far Fields Averaged from the Scalp of Humans*, Brain. 1971; 94(4): p. 681-96, which is hereby incorporated herein by reference.

Electrically evoked Auditory Brainstem Responses (eABR) may be obtained by recording a series of potentials with, in part, one or more scalp electrodes. The response typically occurs within 10 msec after onset of a pulsatile stimulus. The pulsatile stimulus may be provided, for example, by an electrode associated with a cochlear implant or ABI.

In many instances, electrically evoked Auditory Brainstem Responses (eABR) can provide information useful for implants. For example, eABR can provide important information regarding hearing, and using a specific stimuli may provide electrode specific hearing information of a subject. While the CAP measurement can obtain information about nerve fibres within the cochlea, eABR has the ability to check auditory pathway, i.e. assessing the functions of the inner ear, VIII cranial nerves, and various brain functions of the lower part of the auditory system.

For eABR via an ABI, the electrode array is placed directly on the cochlear nucleus, Therefore, the eABR recordings cannot include recordings of waves I, II and partially wave III, and occurs 1-2 ms earlier than it does with a cochlear implant. Since stimulating artifacts are present substantially immediately after the presented stimuli and at the beginning of the recordings, analysis of eABR via ABI is typically more difficult than it is for eABR via a cochlear implant. In the fitting process, for ABI subjects who never heard or have only very little experiences with the hearing (for example, children), eABR becomes a very important objective measurement. Compared to cochlear implant patients, eABR may be of higher importance for ABI patients as some objective measurements often used in the fitting process in cochlear implant patients, may not be elicitable, i.e. electrically evoked stapedial reflex measurement (eSR).

Particular uses of eABR are listed below.

eABR may serve as an aid for the intra-operative or post-operative confirmation of electrode placement, and functionality of the implant (see: Behr R. et al., *The High Rate CIS Auditory Brainstem Implant for Restoration of Hearing in NF-2 Patients*, Skull. Base 17(2), 2007, p. 91-107; and Bahmer A. et al., *Recording of Electrically Evoked Auditory Brainstem Responses (E-ABR) with an Integrated Stimulus Generator in Matlab*, Journal Neuroscience Methods 173(2), 2008, p. 306-314, each of which is hereby incorporated herein by reference. eABR has become a standard measurement for use in judging the proper placement of the electrode paddle on a cochlear nucleus.

eABR may serve an aid for diagnostic assessment of a patient (see Gibson et al., *The Use of Intra-operative Electrical Auditory Brainstem Responses to Predict the Speech Perception Outcome after Cochlear Implantation*, Cochlear. Implants Int., 10 Suppl 1 2009, p. 53-57, which is hereby incorporated herein by reference). In particular, eABR can be a tool for the assessment and monitoring of audiologic, otologic and neurologic disorders (i.e. acoustic tumor monitoring).

eABR may be used as an aid for the post-operative programming of a hearing implantable device, especially in difficult-to-fit patients such as children (see: Brown C. J. et al., *The relationship between EAP and EABR thresholds and levels used to program the nucleus* 24 *speech processor: data from adults*, Ear Hear. 21(2), 2000, and McMahon et al., 2008, p. 151-163; and McMahon C. M. et al., *Frequency-specific Electrocochleography Indicates that Presynaptic and Postsynaptic Mechanisms of Auditory Neuropathy Exist*, Ear Hear. 29(3), 2008, p. 151-163, each of which is hereby incorporated herein by reference).

eABR may provide additional information on psychoacoustic thresholds for each intracochlear or electrode (see Brown et al., 2000)

eABR may be used as an aid to provide quantitative information on auditory pathway (See: Polak M. et al., *Evaluation of Hearing and Auditory Nerve Function by Combining ABR, DPOAE and eABR Tests into a Single Recording Session*, J. Neurosci. Methods 134(2), 2004, p. 141-149; and Gibson et al., 2009).

Obtaining eABRs can be cumbersome. An external system for recording is typically required, which then has to interface/synchronize with the stimulation system. Various recording electrodes need to be positioned on the patient, the location of which may be susceptible to movement by the patient.

Furthermore, commercially available recording systems often record stimuli artifacts together with the physiological response. These artifacts may be much higher than the physiological response (artifacts are up to several decade times higher than a physiological response). Thus, it is often very difficult to judge if the physiological response is present. Sometimes, the artifacts are confused with the physiological response, and thus the final interpretation of the results may lead to an incorrect interpretation. For intraoperative measurement, when relying only on the eABR response, inappropriate judgement may have a very dramatic influence on postoperative performance with the implant system. For eABR recordings, only an alternating artifact cancellation method is being used commercially (for example, see Polak et al., 2004). However, this method is often not satisfactory in cancelling out the stimuli artifacts.

SUMMARY OF THE INVENTION

In accordance with a first embodiment of the invention, a method of measuring electrically evoked auditory brainstem responses of a patient or animal body is provided. The method includes surgically implanting an auditory prosthesis having an electrode array, the electrode array positioned either intracochlear or substantially proximate a brainstem of the body. At least one electrode is stimulated in the electrode array. Electrically evoked auditory brainstem responses resulting from said stimulation are recorded using, at least in part, an electrode in the electrode array, that may be used as a negative electrode, and a electrode positioned proximate the scalp and/or forehead of the body, that may be used as a positive electrode.

In accordance with related embodiments of the invention, the auditory prosthesis may be a brainstem implant or a cochlear implant. The electrode positioned proximate the scalp and/or forehead of the body may be positioned external or internal to the body. The electrode positioned proximate the scalp and/or forehead of the body may be placed substantially proximate the vertex of the head of the body. The electrode positioned proximate the scalp and/or forehead of the body may be operatively coupled to the auditory prosthesis. The auditory prosthesis may include a connector, the method further comprising connecting the electrode positioned proximate the scalp and/or forehead of the body to the auditory prosthesis via the connector. The connector may be positioned internal to the body when implanting the auditory prosthesis, and in connecting the electrode positioned proximate the scalp and/or forehead of the body to the auditory prosthesis via the connector, the electrode positioned proximate the scalp and/or forehead of the body is positioned either internally or externally to the body. The at least one electrode in the electrode array may be used for recording only, or for both recording, and stimulation (i.e., acting as an auditory prosthesis). Stimulating at least one electrode in the electrode array may include stimulating a plurality of electrodes in the electrode array.

In accordance with further related embodiments of the invention, the method may include canceling artifacts from the responses. Canceling artifacts from the responses may include improved forward masking cancellation.

In accordance with another embodiment of the invention, a system for measuring electrically evoked auditory brainstem responses of a patient or animal body includes an auditory prosthesis having an electrode array, the electrode array for positioning either intracochlear or substantially proximate a brainstem of the body. An electrode, which may be used as a positive electrode, is operatively coupled to the auditory prosthesis for positioning proximate the scalp and/or forehead of the body. A controller stimulates at least one electrode in the electrode array, and records electrically evoked auditory brainstem responses resulting from said stimulation using, at least in part, an electrode in the electrode array, which may be used as a negative electrode, and the electrode for positioning proximate the scalp and/or forehead of the body.

In accordance with related embodiments of the invention, the auditory prosthesis may be a brainstem implant or a cochlear implant. The auditory prosthesis may include a connector for connecting to the electrode for positioning proximate the scalp and/or forehead of the body. The connector may removably couple the electrode for positioning proximate the scalp and/or forehead of the body to the auditory prosthesis. The connector may include means for positioning the connector internal to the body when implanting the auditory prosthesis. The controller may simultaneously stimulate at least two electrodes in the electrode array when measuring electrically evoked auditory brainstem responses.

In accordance with further related embodiments of the invention, the controller may cancel artifacts in the responses. The controller may cancel artifacts using improved forward masking cancellation.

In accordance with another embodiment of the invention, a method of measuring electrically evoked auditory brainstem responses of a patient or animal body is provided. The method includes surgically implanting an auditory prosthesis having an electrode array, the electrode array positioned one of intracochlear and substantially proximate a brainstem of the body. At least one electrode is stimulated in the electrode array. Electrically evoked auditory brainstem responses resulting from said stimulation are recorded. Artifacts in the responses are cancelled using improved forward masking methodology.

In accordance with related embodiments of the invention, recording the electrically evoked auditory brainstem responses may include using, at least in part, a positive electrode placed proximate the scalp and/or forehead of the body, and a negative electrode placed substantially proximate one of a mastoid, earlobe and preauricular area of an ear. The positive electrode and the negative electrode may be placed external to the body, and may be, for example, surface electrodes and/or needle electrodes. A ground electrode may be used, and placed, for example, on the lower forehead.

In accordance with further related embodiments of the invention, recording the electrically evoked auditory brainstem responses may include using, at least in part, a positive electrode placed proximate the scalp and/or forehead of the body, and an electrode in the electrode array that acts as a negative electrode. The positive electrode may be operatively coupled to the auditory prosthesis via a connector. The positive electrode may be placed internal or external the body. Stimulating at least one electrode in the electrode array may include stimulating a plurality of electrodes in the electrode array.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments of the invention, a system and method of measuring electrically evoked auditory brainstem responses (eABR) of a patient or animal body is provided. Generally, electrically evoked auditory brainstem responses are recorded using one or more electrodes in a cochlear or auditory brainstem implant's electrode array (e.g., as a negative electrode), and an electrode positioned proximate the scalp or forehead of the patient (e.g., as a positive electrode). Such a configuration advantageously increases the amplitude of the recorded eABR. In various embodiments, artifacts present in the eABR are advantageously cancelled using a forward masking methodology, and/or measurement of the eABR may be performed using a prosthesis without requiring use of a separate recording system. Details are discussed below.

Figure 1A:
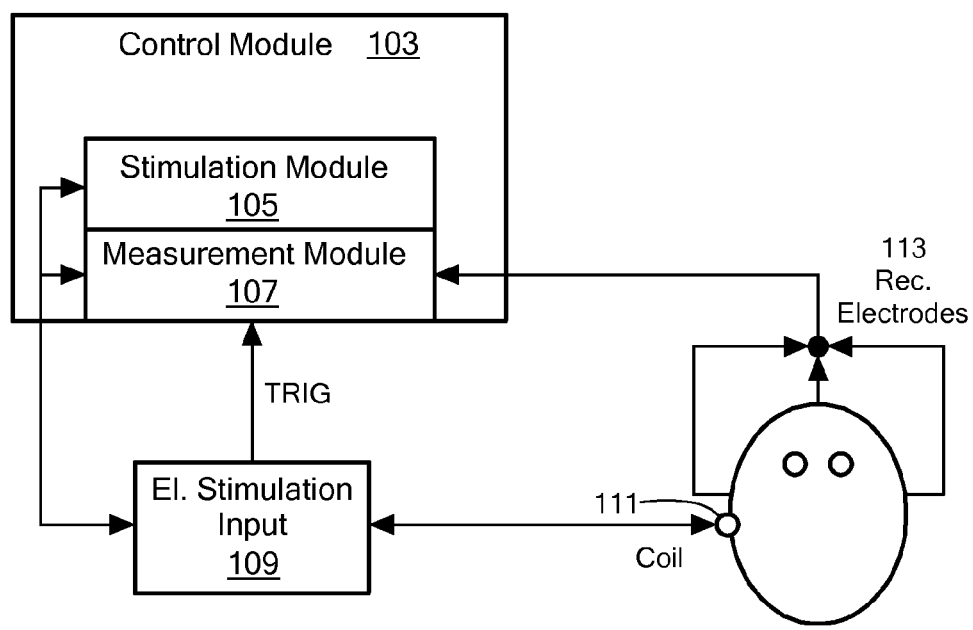
FIG. 1(a) is a block diagram of a conventional system for measuring eABR.
Figure 1B:
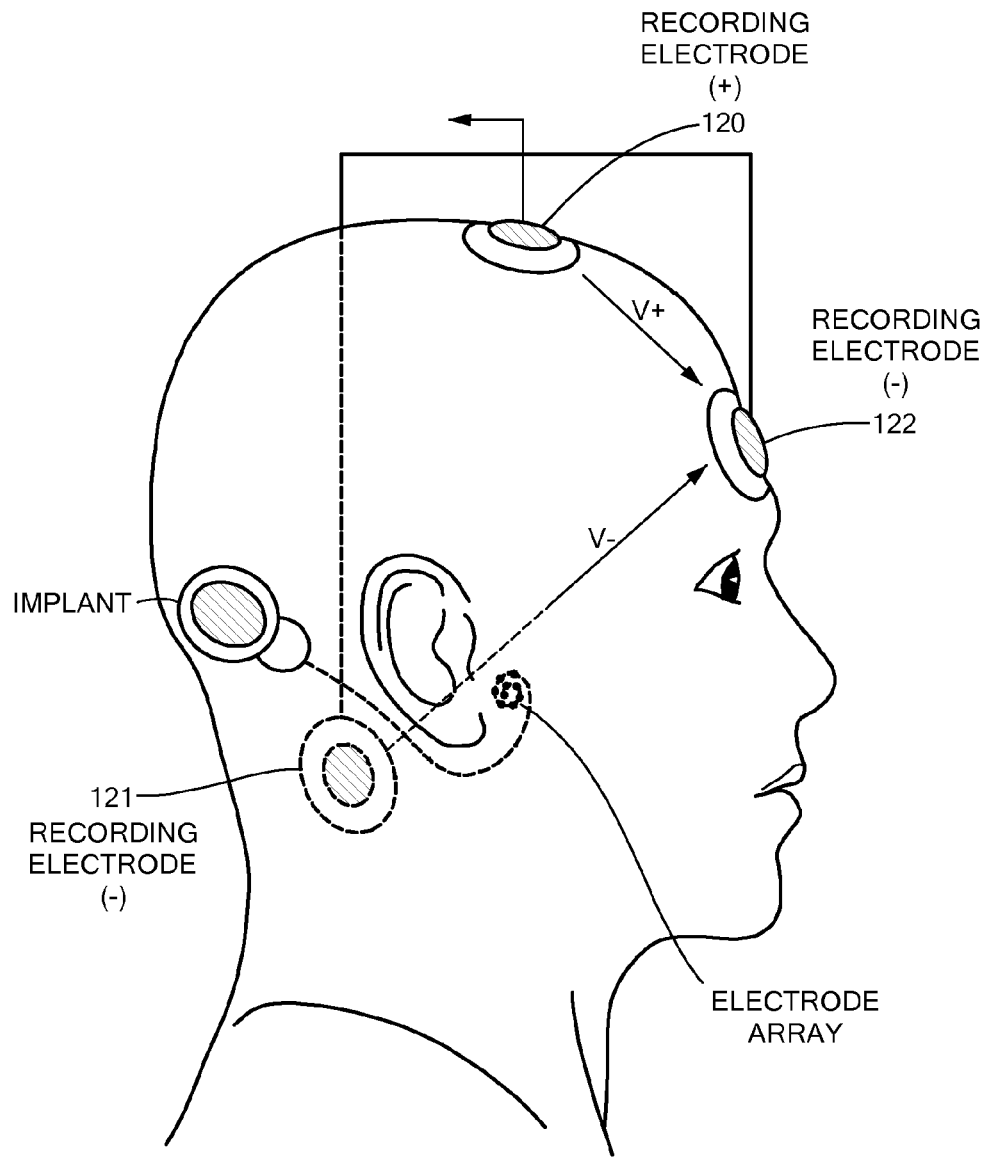
FIG. 1(b) shows typical recording electrode placement for eABR.

FIG. 1(a) is a block diagram of a system for measuring eABR of a patient or animal body. The system includes a control module 101 having, in part, a stimulation module 105 and a recording module 107. The stimulation module 105 provides a stimulation input 109 to the prosthesis (for example, a cochlear implant or an ABI), and communicates triggering information to the recording module 107. Communication between the external and internal portions of the system may be, without limitation, via a transcutaneous radio frequency link, typically involving an external coil 111 that interfaces with an implant's internal coil. Recording electrodes 113 pick up the eABR, which are then processed in the recording module 107. Conventional recording electrode positions for eABR, shown in FIG. 1(b) may include, without limitation, an active positive electrode 120 placed on the vertex (Cz) and/or forehead, and/or an active negative electrode 121 placed on ipsilateral implanted—or contralateral unimplanted mastoid, earlobe or preauricular area of the ear. A reference/ground electrode 122 may be placed either on the neck, lower forehead or shoulder (see, for example, Katz et al., 1994).

Figure 2:
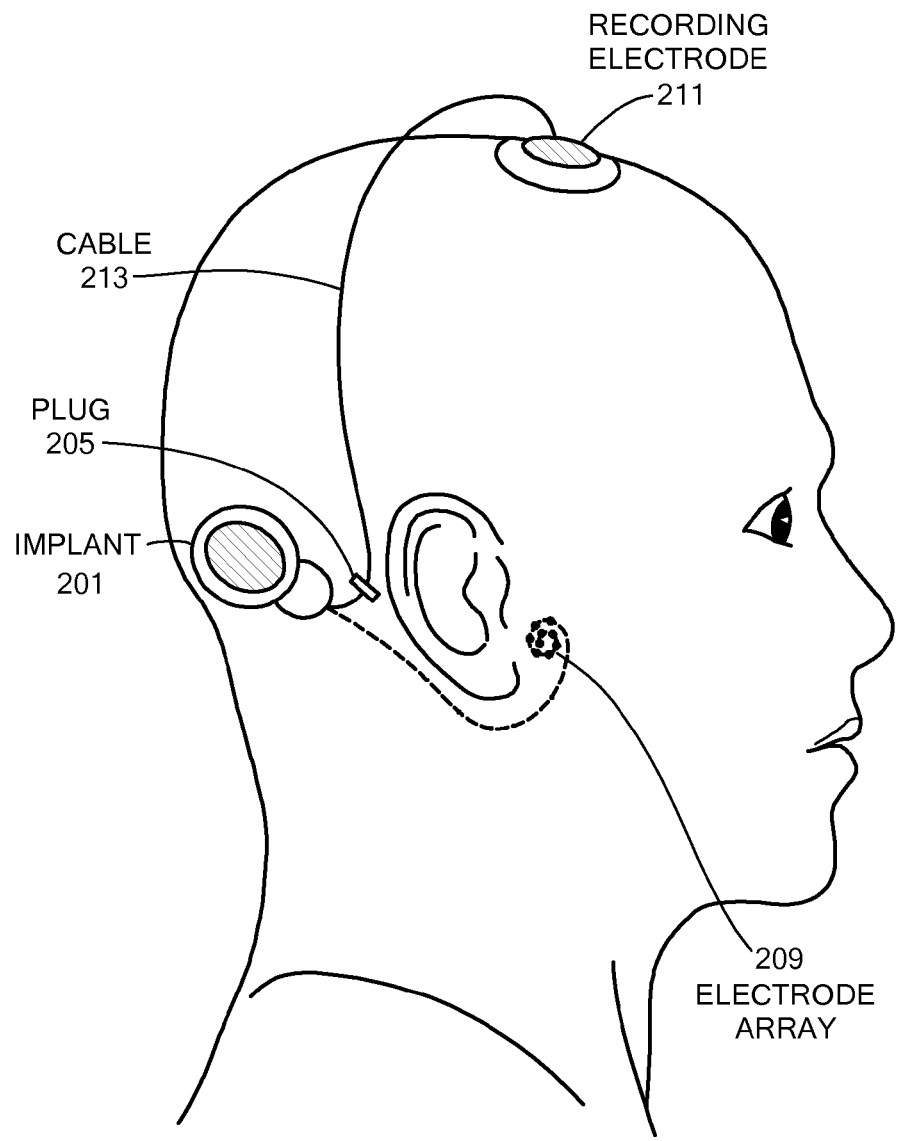
FIG. 2 shows an eABR measuring system, in accordance with an embodiment of the invention.

In illustrative embodiments of the invention, measurement of eABR is performed via the implanted prosthesis, without requiring a separate external recording module. FIG. 2 shows an eABR measuring system, in accordance with an embodiment of the invention. The system includes an implant 201, which may be, without limitation, a cochlear implant or an ABI. The implant 201 includes an electrode array 209 for positioning, without limitation, intracochlear (so as to stimulate the auditory nerve) or substantially proximate a brainstem of the body.

In addition to the electrode array, various recording electrode(s) 211 are connected to the implant 201. Cable/wiring 213, as known in the art, may be used to connect the recording electrode(s) 211 to the implant 201. The cable/wiring may be, without limitation, flexible to allow for adjustment in positioning the electrode 211.

The recording electrode(s) 211 may be removably and/or irremovably connected to the implant 201. In various embodiments, one or more recording electrode(s) 211 may be fully implantable/fixed in position and irremovably connected to the implant 201. In further embodiments, the implant 201 may include a connector(s) 205 that is used to intraoperatively couple one or more recording electrodes 211 to the implant 201. In various embodiments, the plug is positioned internal the patient. After, for example, the intraoperative measurement, the electrode(s) 211 (e.g., the vertex electrode) may then be disconnected, and the implant along with the connector 205 may stay inside the body. Recording electrode(s) 211 may be surface or needle electrodes which are intraoperatively placed (on or just under the skin) and connected to the implant 201 via connector 205. The electrode(s) 211 may then be removed after the evoked potentials measurement. In alternative embodiments, the connector may be positioned external the patient.

In various embodiments of the invention, an electrode 211, for example, and without limitation, a positive electrode, may be positioned on or just under the scalp or forehead of the patient. For example, the electrode 211 may be positioned at the vertex/top of the patient's head. Additionally, one of the electrodes in the electrode array 209 of the implant, positioned intracochlear (for a cochlear implant), or substantially proximate the auditory brainstem (for an ABI), may be used, without limitation, as a negative electrode. This configuration advantageously (and surprisingly) provides more robust eABR measurements compared to previous configurations. The negative electrode 209 may be an already existing electrode in the implant electrode array, such that it is used for stimulation during normal use of the implant, and for recording when measuring eABR. Alternatively, the negative electrode 209 may not be used for stimulation, and hence may need to be added to the existing electrode array configuration of the implant. In accordance with other embodiments of the invention, the implant may attach to a more conventional recording electrode configuration, for example, with the negative electrode positioned for example near the mastoid as shown in FIG. 1(a).

When conducting eABR measurements, a single electrode channel may be activated. Alternatively, a plurality of electrode channels may be activated simultaneously, in accordance with various embodiments of the invention. For example, a plurality of electrodes within the electrode array of a cochlear implant or ABI may be simultaneously activated. Activating a plurality of electrodes simultaneously during eABR advantageously requires lower currents per electrode channel to evoke a response compared to one channel stimulation. Thus, eABR measurements using simultaneous stimulation can be helpful in subjects with higher currents needed for eliciting an auditory perception. Additionally, simultaneous stimulation during eABR allows for a generally faster fitting procedure (i.e., a decreased fitting time) than measuring of evoked responses with one channel stimulation. The fitting map may also be more precise than the approximated fitting map created from the same number of recordings with just one channel stimulation. In difficult-to-fit patients, using multi-channel stimulation responses is generally more robust and easier to recognize than responses when using one channel stimulation.

Simultaneous stimulation of electrodes may be advantageously applied, in addition to or in combination with the above-described eABR embodiments, to all evoked potential methodologies useful for fitting of implant prostheses. Such methodologies may include, without limitation: early latency evoked auditory responses (e.g., eABR); middle latency evoked auditory responses (e.g., MLR, 40 Hz) or late evoked auditory response (e.g., P300, P1N1P2) and muscle reflex responses (e.g., PAMR).

An exemplary methodology/implementation of multi-channel stimulation of evoked potentials/muscle reflexes for fitting an implant is now described. The methodology may be applied to any evoked potential procedure used for the fitting of an implant prosthesis.

1. Select number of channels n being stimulated at the same time. The selected electrodes should be in order; for example, if n=3, electrodes 1-3 are stimulated, followed by electrodes 4-6, electrodes 7-9, electrodes 10-12 . . . .

2. Measure the eABR response (the stimulating level is increased until a clear response is seen).

Figure 3:
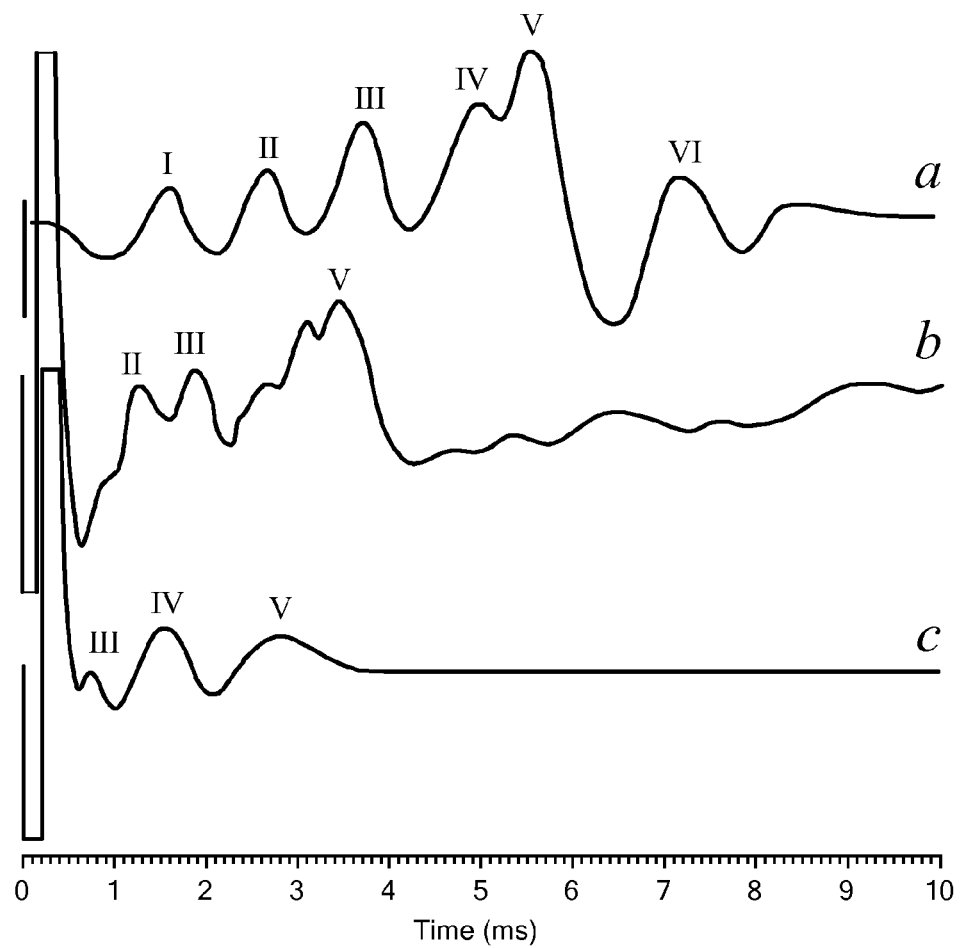
FIG. 3(a-c) shows exemplary ABR and eABR waveforms.

3. Decrease the stimulating level and determine the stimulation level at which the objective response disappears. This stimulation level at which the objective response disappears is called the Threshold Reference (TR). For eABR, Wave 5 is usually observed as it is most robust. FIG. 3(a-c) shows exemplary ABR and eABR waveforms. More particularly, FIG. 3(a) shows an exemplary acoustically evoked ABR; FIG. 3(b) shows an exemplary electrically evoked ABR for a cochlear implant subject; and FIG. 3(c) shows an example of an electrically evoked ABR for an ABI subject.

4. Determine mean Most Comfortable Level (MCL) for the selected group of electrodes. The mean MCL for the selected group of electrodes can be calculated, based on, without limitation, the equation TR/0.6 n.

5. Determine the mean Threshold (T) for the selected group of electrodes. The mean T can be calculated, without limitation, based approximately on the equation TR/2.4 n (25% of the MCL, or four times lower than the MCL).

6. Select the next group of electrodes (electrodes (n+1, . . . , 2 n) and repeat steps 2-5. For example, if n=3, electrodes 4, 5 and 6 are selected.

7. When all the electrodes have been selected, stop measurements.

8. Determine approximate MCL for each single electrode. Using a linear approximation, the approximate MCL can be calculated based on, without limitation, the following equations:

$$n = 4 \text{ (even)}$$

$$E1MCL = MCLGroup1 + (n/2)*(MCLGroup1 - MCLGroup2)/n$$

$$E2MCL = MCLGroup1 + (n/2 - 1)*(MCLGroup1 - MCLGroup2)/n$$

$$E3MCL = MCLGroup1 - (n/2 - 1)*(MCLGroup1 - MCLGroup2)/n$$

$$E4MCL = MCLGroup1 - (n/2)*(MCLGroup1 - MCLGroup2)/n$$

$$E5MCL = MCLGroup2 + (n/2)*(MCLGroup1 - MCLGroup2)/n$$

$$E6MCL = MCLGroup2 + (n/2 - 1)*(MCLGroup1 - MCLGroup2)/n$$

$$E7MCL = MCLGroup1 - (n/2 - 1)*(MCLGroup2 - MCLGroup3)/n$$

$$E8MCL = MCLGroup1 - (n/2)*(MCLGroup2 - MCLGroup3)/n$$

$$\vdots$$

$$n = 3 \text{ (odd)}$$

$$E1MCL = MCLGroup1 + (MCLGroup1 - MCLGroup2)/3$$

$$E2MCL = MCLGroup1$$

$$E3MCL = MCLGroup1 - (MCLGroup1 - MCLGroup2)/3$$

$$E4MCL = MCLGroup2 + (MCLGroup1 - MCLGroup2)/3$$

$$E5MCL = MCLGroup2$$

$$E6MCL = MCLGroup2 - (MCLGroup2 - MCLGroup3)/3$$

$$\vdots$$

Determine approximate Threshold T for each single electrode. Using a linear approximation, the approximate T can be calculated based on, without limitation, the following equations:

$$n = 4 \text{ (even)}$$

$$E1T = TGroup1 + (n/2)*(TGroup1 - TGroup2)/n$$

$$E2T = TGroup1 + (n/2 - 1)*(TGroup1 - TGroup2)/n$$

$$E3T = TGroup1 - (n/2 - 1)*(TGroup1 - TGroup2)/n$$

$$E4T = TGroup1 - (n/2)*(TGroup1 - TGroup2)/n$$

$$E5T = TGroup2 + (n/2)*(TGroup1 - TGroup2)/n$$

$$E6T = TGroup2 + (n/2 - 1)*(TGroup1 - TGroup2)/n$$

$$E7T = TGroup1 - (n/2 - 1)*(TGroup2 - TGroup3)/n$$

$$E8T = TGroup1 - (n/2)*(TGroup2 - TGroup3)/n$$

$$\vdots$$

$$n = 3 \text{ (odd)}$$

$$E1T = TGroup1 + (TGroup1 - TGroup2)/3$$

$$E2T = TGroup1$$

$$E3T = TGroup1 - (TGroup1 - TGroup2)/3$$

$$E4T = TGroup2 + (TGroup1 - TGroup2)/3$$

$$E5T = TGroup2$$

$$E6T = TGroup2 - (TGroup2 - TGroup3)/3$$

$$\vdots$$

In various embodiments, T levels may not be calculated, or T for each electrode may be obtained, for example, based on T=0.1 (MCL). The above-described equations assume that the electrodes being stimulated are properly inserted in the cochlea. If any of the electrodes is malfunctioning or extra-cochlear, these electrodes should be excluded from the stimulation, and the MCL and T calculations adjusted accordingly. The above-described methodology is applicable to eCAP, in which case TR is defined as the maximum stimulating level at which no CAP response is elicitable. The calculations of MCL and T may need to be appropriately adjusted to account for various types of simulation properties of an implant prosthesis. In various embodiments, the constant value of 0.6 and 2.4 in the calculation of the MCL group (TR/0.6n) and T group (TR/2.4n) may be different for different electrode arrays.

In further illustrative embodiments of the invention, artifact cancellation by subtraction methodologies is applied to eABR measurements. In preferred embodiments, the so called "improved forward masking method" may be utilized, similar to that used for the recording of CAP responses, but never before applied to eABR measurements (see Miller C. A. et al., *An improved method of reducing stimulus artifact in the electrically evoked whole-nerve potential*, Ear Hear. 2000 August; 21(4), p. 280-90 at FIG. 2, which is hereby incorporated herein by reference). eCAP recordings are sensitive to stimuli artifacts, electrode or implant artifacts and miogenic type artifacts. In addition to the above mentioned artifacts for eCAP, eABR is very sensitive to artifacts caused by patients (i.e. patient's movement) and their surroundings. The above-described embodiments allow for more stable electrode placement (in particular, embodiments in which the recording electrodes are implanted or otherwise fixed in position), leading to more favourable cancellation using subtraction methodology.

Figure 4:
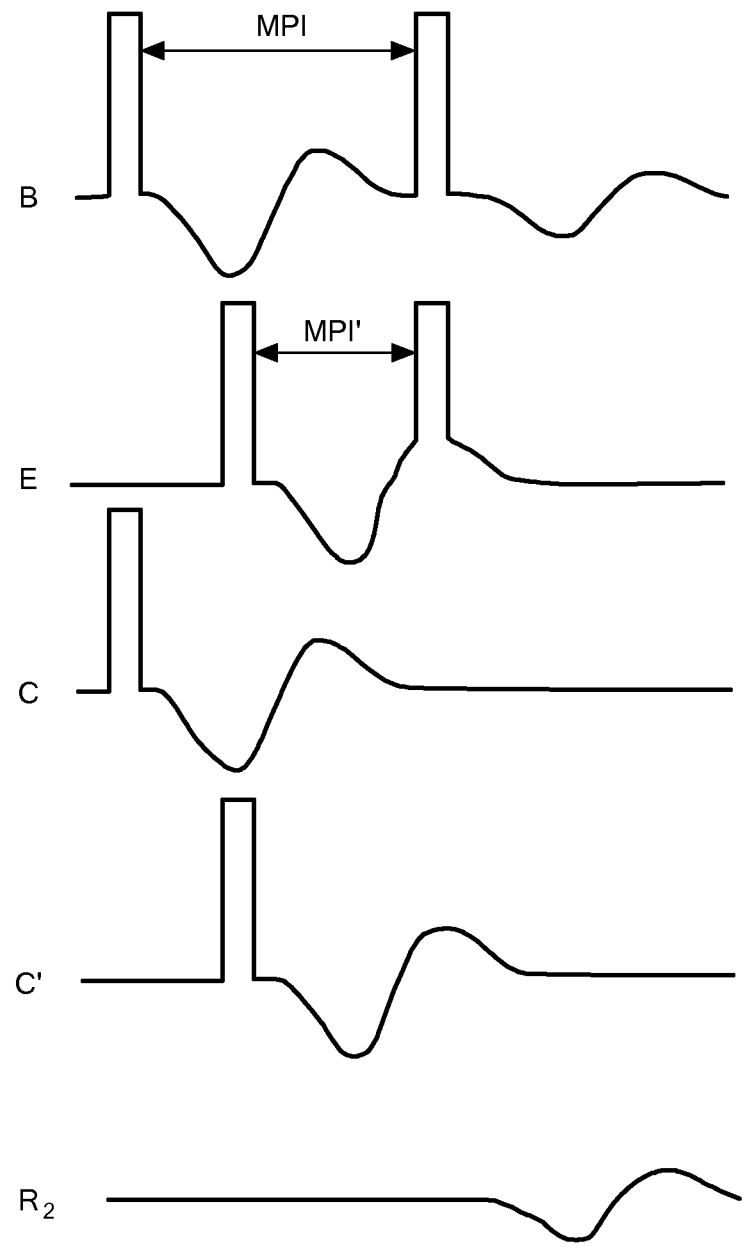
FIG. 4 shows an improved forward masking scheme for applying to an eABR measurement, in accordance with an embodiment of the invention.

FIG. 4 shows an "improved forward masking" scheme for applying to an eABR measurement, in accordance with an embodiment of the invention. It is to be understood that use of other mathematical artifact cancellation methodologies, as known in the art, such as the subthreshold template methodology or standard forward masking methodology may also be utilized. Illustratively, with reference to FIG. 4, a probe-alone condition is not recorded (thus, the assumption in standard forward masking methodology that the morphology of the partially masked EAP is identical to that of the unmasked EAP is no longer needed). Instead, direct measurement of the EAP to a masked probe at various masker-probe intervals are taken. In FIG. 4, trace B shows a stimulus that elicits a partially refractory response. As shown in Trace E, the probe artifact in B is subtracted by recording the forward-masked probe using a masker-probe interval having absolute refractoriness (E). To eliminate the masker stimuli introduced in B and E, recordings of the masker response C and a time-shifted masker response C' are utilized. The resultant waveform ($R_2$), equal to B−E−C+C' has eliminated the probe stimulus artifact.

Advantages of using the above-described implant recording system with electrodes for CI and ABI subjects include: improved artifact cancellation; less sweeps for each recording will result in decreased clinical time/faster recordings; the recording electrode configuration of eABR recordings described in the above embodiments will decrease artifacts caused by patient (i.e. patients movement), particularly where fixed electrodes are used; less sensitivity to possible errors, particularly where stimulating and recording electrodes have fixed positions—subjects will have more freedom to move during the measurement; and it is easier to perform (no need of an external system for recording, no need to connect both recording system and system for stimulation, and no need to place the recording electrodes (in embodiments where electrodes are fixed in position).

It is to be understood that the above-described embodiments may be used for other types of electrically evoked potentials (EEP) measurements (e.g., including early, middle and late latency auditory responses), however, the placement and number of the recording electrodes may differ in dependency on what type of EEPs is being measured. For example, when measuring late latency potentials, additional Cz electrodes may be added.

Embodiments of the invention may be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention.

What is claimed is:

1. A method of fitting an auditory prosthesis using electrically evoked auditory brainstem responses of a patient or animal body, the prosthesis including an electrode array, the electrode array divided into a plurality of predefined groups, the method comprising:
   simultaneously stimulating the predefined group of electrodes at a stimulation level;
   for each predefined group of electrodes,
      increasing the stimulation level until a measured evoked auditory brainstem response is observed using an electrode positioned proximate the scalp and/or forehead of the body;
      decreasing the stimulation level to determine the Threshold Reference (TR) stimulation level at which the measured evoked auditory brainstem response disappears; and
      determining, based at least in part on Threshold Reference (TR), at least one parameter selected from the group consisting of a mean Most Comfortable Level (MCL) and a mean Threshold (T) for the predefined group of electrodes;
   determining at least one parameter selected from the group consisting of Most Comfortable Level (MCL) and Threshold (T) for each electrode in the electrode array; and
   fitting the auditory prosthesis with the at least one parameter selected from the group consisting of Most Comfortable Level (MCL) and Threshold (T) for at least one electrode in the electrode array.

2. The method according to claim 1, wherein the auditory prosthesis is one of a cochlear implant and a brainstem implant.

3. The method according to claim 2, wherein increasing the stimulation level until a measured evoked auditory brainstem response is observed includes using an electrode positioned proximate the scalp and/or forehead of the body.

4. The method according to claim 3, wherein the electrode positioned proximate the scalp and/or forehead of the body includes placing the electrode substantially proximate the vertex of the head of the body.

5. The method according to claim 3, wherein the electrode positioned proximate the scalp and/or forehead of the body is connected to the auditory prosthesis via wire.

6. The method according to claim 1, wherein the electrodes in the electrode array are sequentially ordered relative to their position with the electrode array, and wherein the electrodes within the predefined groups of electrodes are in a sequential order.

7. The method according to claim 1, wherein each predefined group of electrodes includes the same number of electrodes, and wherein each electrode is associated with only one group of electrodes.

8. The method according to claim 1, wherein each predefined group of electrodes has N number of electrodes, and wherein determining the mean Most Comfortable Level (MCL) is based on the equation: mean MCL=TR/((a constant value)N).

9. The method according to claim 8, where the constant value is 0.6.

10. The method according to claim 1, wherein each predefined group of electrodes has N number of electrodes, and wherein determining the mean Threshold (T) is based on the equation: T=TR/((a constant value)N).

11. The method according to claim 10, wherein the constant value is 2.4.

12. The method according to claim 1, wherein each predefined group of electrodes has N number of electrodes, and wherein determining the mean Threshold (T) is based on the equation: T=0.1MCL.

13. The method according to claim 1, wherein determining at least one parameter selected from the group of parameters consisting of Most Comfortable Level (MCL) and Threshold (T) for at least one electrode in the electrode array includes using a linear approximation.

* * * * *